United States Patent [19]

O'Brien

[11] Patent Number: 4,654,794
[45] Date of Patent: Mar. 31, 1987

[54] METHODS FOR DETERMINING THE PROPER COLORING FOR A TOOTH REPLICA

[75] Inventor: John K. O'Brien, Sudbury, Mass.
[73] Assignee: Colorgen, Inc., Billerica, Mass.
[21] Appl. No.: 580,864
[22] Filed: Feb. 18, 1984
[51] Int. Cl.$^4$ .................. G06F 15/42; A61C 13/08; A61C 19/10
[52] U.S. Cl. .................. 364/413; 364/415; 433/26; 433/203.1
[58] Field of Search ........... 364/400, 413, 415, 417, 364/148-150, 167-168; 433/25-27, 54-55, 171, 201-203, 213, 215, 229

[56] References Cited

U.S. PATENT DOCUMENTS

| | | | |
|---|---|---|---|
| 3,436,157 | 4/1969 | Adler et al. | 433/26 X |
| 3,507,042 | 4/1970 | Hana | 433/26 X |
| 3,555,262 | 1/1971 | Schimada | 235/193 |
| 3,748,741 | 7/1973 | Yerkes, Jr. | 433/203 X |
| 3,778,541 | 12/1973 | Bowker | 178/5.2 R |
| 3,935,436 | 1/1976 | Holschlag et al. | 235/151.35 |
| 3,999,045 | 12/1976 | Schwartz et al. | 235/151.1 |
| 4,115,922 | 9/1978 | Alderman | 433/26 X |
| 4,207,678 | 6/1980 | Jeannette | 433/203 |
| 4,290,433 | 9/1981 | Alfano | 433/25 X |
| 4,324,546 | 4/1982 | Heitlinger et al. | 433/25 |
| 4,382,784 | 5/1983 | Freller | 433/26 |
| 4,411,626 | 10/1983 | Becker et al. | 364/168 X |
| 4,505,589 | 3/1985 | Ott et al. | 356/402 |

OTHER PUBLICATIONS

W. Culpepper, "A Comparative Study of Shade—Matching Procedures", vol. 24, No. 2, *J. Pros. Dent.*, Aug. 1970, pp. 166–173, Emory Univ., Atlanta, Ga.
D. McMaugh, "A Comparative Analysis of the Colour Matching Ability of Dentists, Dental Students, and Ceramic Technicians", *Australian Dental Journal*, Jun. 1977, vol. 22, No. 3, pp. 165–167.
S. Bergen et al., "Dental Operatory Lighting and Tooth Color Discrimination", *JADA*, vol. 94, Jan. 1977, pp. 130–134.
R. Sproull, "Color Matching in Dentistry, Part I, The Three-Dimensional Nature of Color", *J. Prosthet. Dent.*, vol. 29, No. 4, Apr. 1973, pp. 416–422.
R. Sproull, "Color Matching in Dentistry, Part II, Practical Applications of the Organization of Color", *J. Prosthet. Dent.*, vol. 29, No. 5, May 1973, pp. 556–566.
R. Sproull, "Color Matching in Dentistry, Part III, Color Control", *J. Prosthet. Dent.*, vol. 31, No. 2, Feb. 1974, pp. 146–154.
W. Wozniak et al., "How to Improve Shade Matching in the Dental Operatory", *JADA*, vol. 102, Feb. 1981, pp. 209–210.
D. Tompkins, "Computer Color Matching Makes Sense Even for Small Processors", *Plastics Engineering*, Jun. 1979, pp. 29–31.
"Color-Measuring Instruments: An NPE Highlight", *Process Engineering News*, 1976, pp. 21, 23, 125.
M. Jorgenson et al., "Spectrophotometric Study of Five Porcelain Shades Relative to the Dimensions of Color, Porcelain Thickness, and Repeated Firings", *Journal of Prosthetic Dentistry*, vol. 42, No. 1, Jul. 1979, pp. 96–105.

*Primary Examiner*—Gary V. Harkcom
*Attorney, Agent, or Firm*—Joseph S. Iandiorio; Douglas E. Denninger

[57] ABSTRACT

Polychromatic light is directed at the surface of a live tooth and color data of light reflected therefrom is recorded, multiplied by the stored power distribution of a first standard illuminant and converted to three tristimulus values. Such values are compared with color values of a first group of stored color dental shades, and if a match occurs within a given tolerance, an indication of the nature of the recipe is produced. A second level search may be carried out against a substantially larger group of stored dental shades in the event of a no-match condition resulting from the first search. Excellent lifelike reproduction of the patient's tooth is enhanced by checking for least metamerism by operating upon the measured data with other illumination standards and selecting the best match under all lighting conditions. Additionally, a translucency factor is calculated, and employed to reduce the opacity of the inner opaque layer of the recipe which would otherwise be indicated should the patient's tooth not have a high degree of translucency. The calculation of a fluorescence factor also enhances excellent reproduction of the live tooth, and is employed to indicate the addition of a fluorescent ingredient to the final recipe.

21 Claims, 3 Drawing Figures

METHODS FOR DETERMINING THE PROPER COLORING FOR A TOOTH REPLICA

BACKGROUND OF THE INVENTION

The present invention relates to the field of replacing a patient's tooth with a replica thereof.

During the process of replacing a lost tooth, the task of the dentist, working with a dental laboratory, is to produce a good visual match between the patient's original tooth and the replica made up by the laboratory. To date, there has been no really accurate shade matching capability in the dental field. Various devices employed by the dentists to attain this match involve use of a red, green and blue colorimeter, a visual matching comparator, and the standard set of acrylic or porcelain shade tabs used by virtually every dentist practising in the crown and bridge field. It is thus highly desirable to provide a method for accurately measuring the shade value of a tooth within the mouth of the patient and use the data resulting from the measurement of such tooth to select a matching recipe which appears under all lighting conditions to be reasonably close to the appearance of the original tooth. In the past, considerable inaccuracy in this matching process has resulted from essentially subjective evaluation of the dental color of the tooth. The dentist examines the tooth under variable lighting conditions which results in substantial errors in this matching process and, additionally, dentists are often color blind so that the resulting data sent to the laboratory technician is quite inaccurate.

SUMMARY OF THE INVENTION

It is thus a principal object of the present invention to provide a rapid and economical method for deriving data from the examination of a tooth within the patient's mouth and using such data to objectively obtain a porcelain recipe which visually matches the appearance of the patient's live tooth, particularly under variable lighting conditions.

It is a further object of the present invention to provide a method of searching a large group of porcelain recipes present in electronic storage and to select with great accuracy those recipes which will be closest to the patient's live tooth with regard to visual appearance.

It is a further object of the present invention to produce results previously unobtainable through use of translucency and fluorescence factors of a particular patient's tooth.

It is a further object of the invention to provide a method for indicating a porcelain recipe which will appear to be a truly lifelike replica of the patient's tooth.

In accordance with a preferred method of the present invention, polychromatic light is directed at the surface of the tooth in the patient's mouth, color data of light reflected therefrom is recorded and multiplied by the stored power distribution of a first standard illuminant and is thereafter converted to three tristimulus values which are, in turn, compared with the color values of a first group of stored major color dental shades. If a match occurs within a given tolerance, the identification of the selected matched porcelain color shade and given available types of ingredients is produced, for use in preparing a matched replica of the live tooth. If a match is not produced, a second level search is carried out against a substantially larger group of stored dental shades, and if a match still does not occur, tolerances may be loosened to effect a match. Optionally, a stored color shade value may be modified in color space to bring it within the tolerance value to effect a match, and such modification may be advantageously employed to alter the color shade value of an ingredient of the indicated matched recipe, to an extent proportional to such modification. Matching is enhanced by checking for least metamerism in the event that two or more color data matches are produced, by operating upon the three tristimulus values with one or two other illumination standards. The translucency factor of the live tooth is calculated and employed, in the event that it is above a certain level, to reduce the opacity of the indicated inner opaque layer of the recipe to increase visual fidelity of the match. Additionally, the florescence factor of the tooth is calculated and employed to indicate the addition of a suitable amount of fluorescent ingredient to the recipe to further aid in the fabrication of a lifelike replica of the patient's tooth.

Other objects, features and advantages of the present invention will become apparent upon study of the following detailed description taken in conjunction with the drawings.

DETAILED DESCRIPTION

Figure 1:
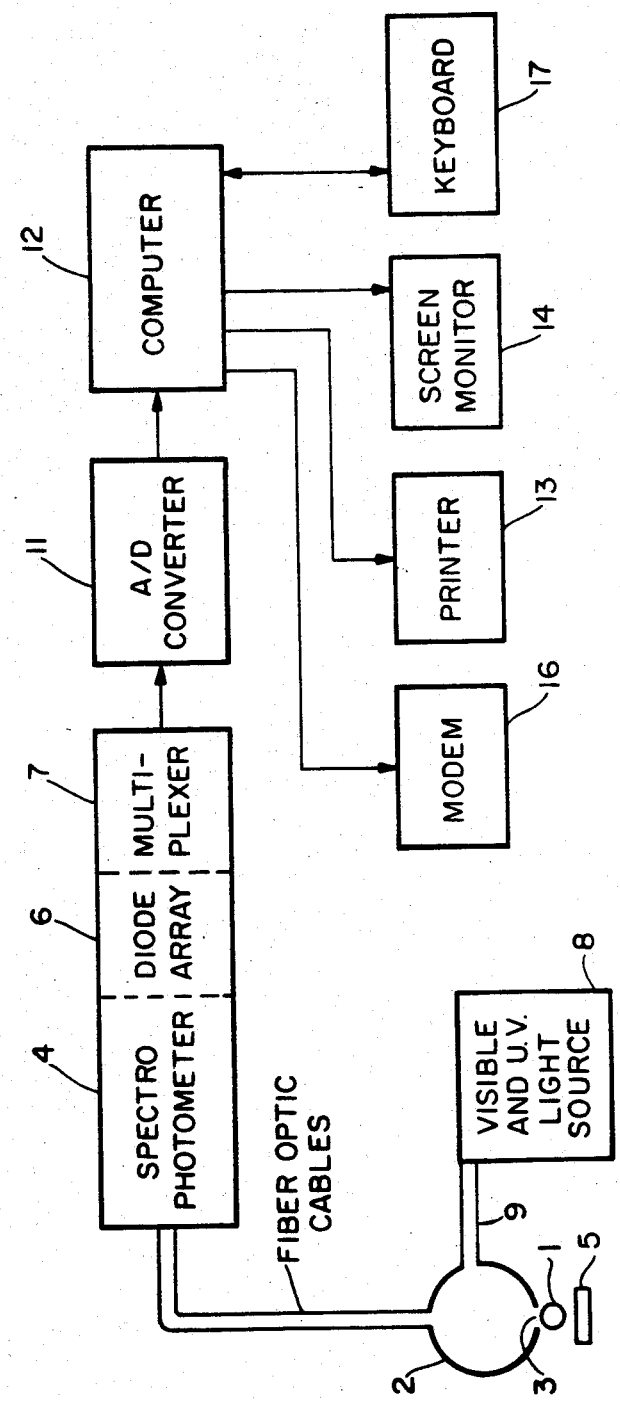
FIG. 1 illustrates an arrangement of components which may be employed to carry out the method of the invention.

Referring now to FIG. 1, a live tooth 1 in the mouth of the patient is schematically illustrated, and a port 3 is formed within the wall of a light integrating sphere 2. The inside surface of the sphere is coated with white matt paint to thereby sharply reduce spectral reflections of light, which reflections produce serious distortions in the reading of the color data of the tooth. A flash light source 8 is provided, coupled to sphere 2 via fiber optic cable 9. The light introduced into the sphere is directed by the inside diffusely light reflecting walls at tooth 1 from all directions, and the reflecting light is read by spectrophotometer 4, which functions to produce electrical signals indicative of the strength of the reflected light in sixteen different band widths. The polychromatic light re-emitted by 1 is broken up by the spectrophotometer by means of a grating or other well-known device for this purpose and the resulting frequency components thereof are directed at a diode array section 6 within the spectrophotometer. Each diode produces an electrical signal having an amplitude proportional to the amplitude of the reflected light within its associated band width. This apparatus is well-known to those skilled in the art and is also termed a monochronomator. One form of such a device is described in column 2 of U.S. Pat. No. 3,935,436. In the device employed by the inventor, the frequency spectrum is broken up into sixteen bands of approximately 20 nanometers so that each photodiode detects a small segment of the visible spectrum. The multiplexer (parallel to serial) section 7 of unit 4 is coupled to analog to digital converter 11 which converts the multiplexed analog signals into digital words which are applied to computer 12.

Digital computer 12 carries out a number of the functions of the method of the invention to be described below, and controls the operation of printer 13 and a CRT screen monitor 14 and, optionally, a modem 16 for communicating with more distant points. Keyboard 17 is also coupled to computer 12 to call up various menus and otherwise input date thereto. The computer functions to normalize the dental color data obtained by measuring reflected light off of the tooth by applying a correction factor to compensate for any parameter changes such as in the color signature of the light source. The computer operates on the resulting color data with the stored power distribution of a given standard illuminant, through multiplication, converts the modified color data to three tristimulus values, compares the resulting values with stored color values of groups of dental shades, and identifies the matched shades to produce a printout of information by printer 13 indicative of the recipe to be employed. The computer also checks for least metamerism, employs a translucency factor to obtain a better match, derives a fluorescence factor to aid in the matching process and has other functions explained below in greater detail.

Figure 2:
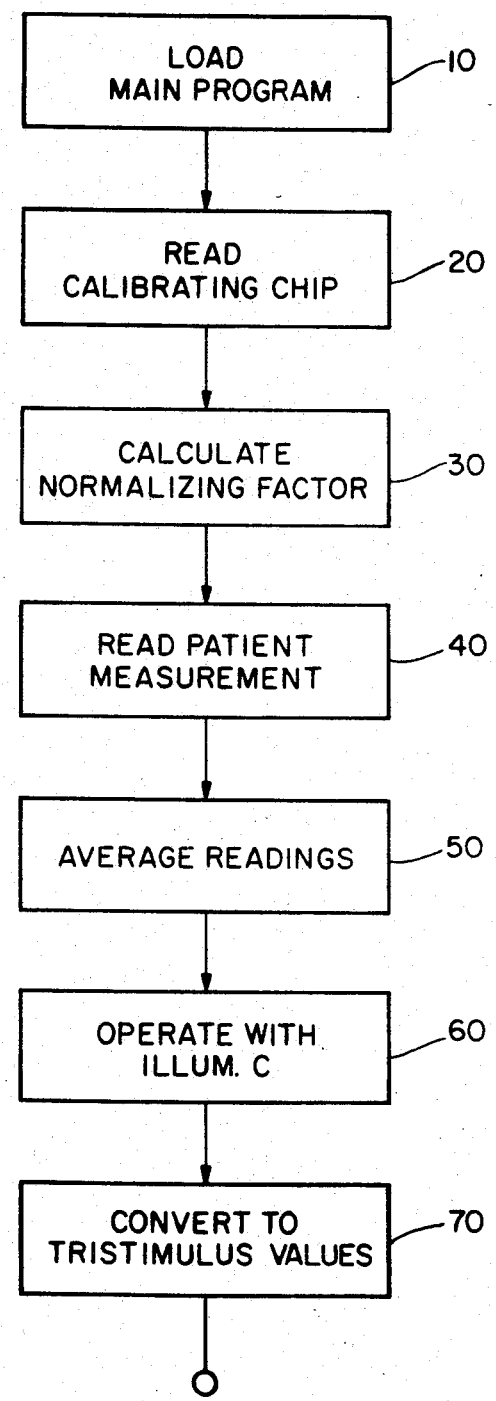
FIGS. 2 and 3 illustrate flow charts helpful in understanding the steps of the method.

The first step is to actuate keyboard 17 to load the main program, such step being represented by block 10 in FIG. 2. A standard color calibration chip is employed to calibrate the system and is placed directly over access port 3, light source 8 is actuated and a digital reading is made of the reflectance color signature of the chip which is transmitted by the spectrophotometer and A/D converter 11 to computer 12. Thus, color data is recorded consisting of a plurality of binary words indicative of the power distribution of wavelengths of light reflected from the chip within each of a plurality of frequency bands. The normalization of subsequent reflective color data measurements of the tooth is enabled by applying a correction factor thereto, produced by subtracting data recorded upon the illumination of the calibration chip from the stored set of data representing the calibration of the stored dental color data base in computer 12. The normalization of data produced by the illumination of the live tooth is important since drifts in parameters of the apparatus during use must be compensated for. For example, a variation in the frequency signature of light produced by light source 8 would produce erroneous readings and hence inhibit good matching. Preferably, the step of illuminating the calibration chip should be frequently performed before reading the reflectance data from the live tooth in order to maintain the normalization. These steps are represented by blocks 20, 30 and 40 in FIG. 2.

Block 50 indicates the step of averaging the reading of several measurements in order to reduce signal to noise ratios and hence reduce overall reading errors. Such a step is optional but preferred.

The next step, indicated by block 60, is to operate upon the color data, previously normalized, recorded from the measurement of the patient's tooth, by multiplying such data with the stored power distribution curve of a given standard illuminant such as illuminant 'C'. Such multiplication is performed digitally by multiplying individually the above mentioned sixteen channels across the wavelength spectrum.

Block 70 indicates the step of converting the resulting data to tristimulus values. Tristimulus values are basically numerical representations of red, green and blue values of the color shade being processed. They are produced by multiplication of the reflectance values derived from step 60, with three different sets of CIE determined standards which approximate, as nearly as possible, the perfect red, green and blue curves over the visible spectrum. The result of the latter multiplication is three specific values which are representative of the area under the product curve of the CIE tables with the normalized reflectance curve being processed. The resulting unique tristimulus values represent the color of the patient's tooth. It is, however, within the scope of the present invention to match without conversion to tristimulus values, by employing straight reflectance values. However, the algorithms needed to perform such a process are far more complex. Thus, the tristimulus value conversions are performed under a given illuminant such as illuminant 'C' which is a series of tabulated values determined by international convention to represent most appropriately power frequency distribution of an incandescent lamp. The patient's color coordinate data for his live tooth under examination, as it would appear under illuminant 'C' conditions, is now employed to perform the search to determine which stored shade will produce the best match.

In accordance with the preferred method of the invention, different search levels are provided. The first level consists of searching data indicative of 16–25 main shades throughout dental color space. A given tolerance is established to determine whether or not a match is present; that is, the maximum acceptable difference in color between the patient's measurement data and the actual dental shade in the library, which is calculated by means of color difference equations which are standard mathematical formulae used to calculate the dimensional discrepancy in color space between a given shade and a shade that is stored. These color difference equations are well established protocols that have been agreed upon by international convention. They are known as the CIE $L^*u^*v^*$ or the 1976 CIE $L^*a^*b^*$ Color Difference Equations. See pages 78–110 of PRINCIPLES OF COLOR TECHNOLOGY, 2nd Edition, Fred Billmeyer, John Wiley, 1981.

Figure 3:
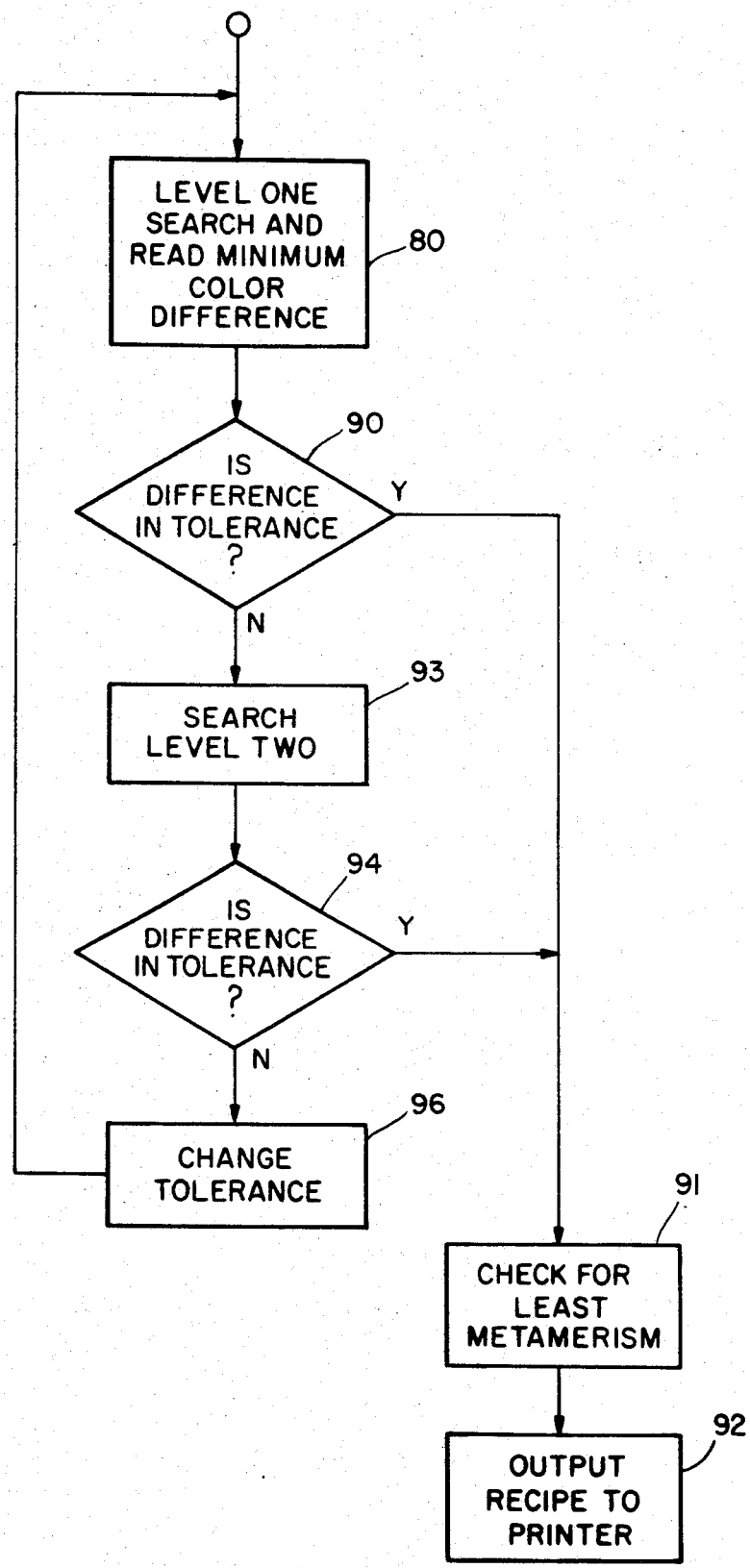

In the level 1 search, the three tristimulus values of the patient's tooth are compared with the tristimulus values of 16–25 main shades, and if the color difference calculated is less than or equal to the tolerance factor inputted to the computer, the computer selects the shades that have the closest match acceptable under tolerance if there are more than one. Since we have employed illuminant 'C' to operate upon the measured tooth data, the matching process will search reference tristimulus dental shade values in storage representative of data determined under the same illumination 'C' standard of incandescent light. In other words, the computer identifies those stored matched color shades which are close enough in color space to the shade represented by the patient's tristimulus values addressing the data bank to satisfy a given tolerance factor. The above-mentioned step is represented by block 80 in FIG. 3. If a shade is not within tolerance, it is necessary to go via 90 to the next level of search indicated by block 93. In the event that one or more stored dental shades are within tolerance, block 91 indicates a check for least metamerism, to be described below, and a recipe may be printed out after such check is performed, as indicated by block 92, indicative of the manufacturer's composition which is associated with the best matched color data in storage.

The second level search is thereafter carried out in the event that a no-match condition has been produced. Such search involves comparing the tristimulus values with a second substantially larger group of stored dental color shades. Such group comprises 100–150 subshades that are "overlaid" over the 16–25 main shades in the same color space. The search proceeds as before and, if a no-match condition still is produced, the above-mentioned tolerance factor may be loosened (block 96) and searches under levels 1 and/or 2 may be carried out again to increase the probability of a successful match. The search routine automatically progresses to the next level if we do not find a match in the level preceding it, and each time an option exists of either tightening or loosening our tolerance levels.

In accordance with an important feature of the invention, if matches are not found by virtue of searching levels 1 and 2, a stored color shade value may be changed in a manner to bring it within the tolerance value and such change is employed to alter the color shade value of the indicated matched recipe ingredient. This step is made possible because the color space surrounding a stored dental shade may change linearly as the point in color space represented by the shade is shifted toward the addressing patient color coordinate. A shift is made to cause the stored data otherwise not in tolerance to become in tolerance and such shift will indicate a corresponding change to be made in the color data of an ingredient of the selected recipe. In other words, we can value certain ingredients in the recipe according to that measurement difference that we obtain through our color difference calculation to bring the recipe close to the target match.

In the event that two or more color data match indications are produced, it is highly desirable to select the best match by checking for least metamerism. This is because while a shade may appear to match under daylight conditions, for example, this same shade might create a substantial mismatch under incandescent illumination conditions. Since one of the objects of this invention is to produce a visually and realistically accurate replica of the patient's live tooth, the similarity of appearance should be attainable over two or even three different lighting conditions. In accordance with this step, represented by block 91 in FIG. 3, the three tristimulus values representing the reflectance of the tooth of the patient is are operated upon with at least one additional illumination standard, such as daylight (D6500), the term "operating on" in this context generally means multiplication. The so modified tristimulus values are matched with a second set of stored reflectance color data of the previously matched shades, but which have been determined under the different daylight illumination standard, rather than standard illuminant 'C'. After this occurs, a determination is made as to which matched shade produces the least color difference under the varying illumination conditions. For example, let it be assumed that both shade 'A' and shade 'B' have been determined to be within tolerance so that they are matched with the data indicative of the patient's tooth as previously described under illuminant 'C' conditions. It may be that the performance of the above-mentioned matching under illuminant 'D' will indicate that shade 'A' is still quite close to the dental color shade being matched, but that shade 'B' is now a considerable distance in color space away from the measured color shade of the patient's tooth. In this case, the computer would produce an indication that shade 'A' is to be employed in fabricating the replica of the tooth rather than shade 'B'. The above method may be expanded by calling up from storage shade data determined under a third illumination standard such as standard 'B' and, in this case, the illumination standard 'B' would be multiplied together with the initial reflectance data representative of the patient's tooth under examination. It may be that one shade, which will be ultimately selected, remains close in color space to the addressing dental color shade under all three lighting conditions and the remaining matched stored shades do not do so. The foregoing may be accomplished by storing the various dental shades to be searched in three groups, each group representing the shades determined under the various international illumination standards.

The production of a replica of a patient's tooth which gives excellent visual matching under various lighting conditions is further enhanced in accordance with the method of the invention by producing a transclucency factor which is assignable to the search. Basically, the recipe consists of successive build-ups in a prearranged selection of inner opaque, body, and outer incisal procelain layers. If a patient has a high degree of translucency associated with his tooth, it is desirable to select an opaque shade for the inner layer which more appropriately matches the color of the patient's tooth since the influence of the opaque layer will be increasingly dominant in the final recipe as translucency increases. Hence, a recipe that we may have normally selected in accordance with the above-described searches, might not be adequate to convey a good color effect to match the patient's natural dentition. Thus, the translucency factor, if considerable, may be employed in accordance with the invention, to print out an indication of a lighter opaque shade for the inner structure which would be different than the one automatically included in the recipe.

The translucency factor is derived by placing a black backing 5, shown in FIG. 1, in back of the tooth 1, illuminating the black backing and recording the reflected color data from the tooth. The resulting data is subtracted from the data derived from illuminating the tooth without a black backing, and the result is a value which is proportional to the degree of translucency of the tooth. Should the tooth have a low degree of translucency, the black background would have little influence upon the reflective date, whereas the opposite would be true should the tooth have a high degree of translucency. The resulting translucency factor may be employed to address a look-up table in the computer which would, in turn, produce data indicative of modification of the opacity factor. Should the translucency factor exceed a predetermined value, the look-up table would generate data indicative of a reduction in the opacity factor data component of the recommended matched recipe. As a result of the foregoing, the final replica will have a degree of simulated translucency which more accurately corresponds to the translucency of the live tooth under examination.

In order to further my objective of producing excellent visual matching between the replica and the patient's tooth, a fluorescence factor is produced which is proportional to the degree of natural fluorescence of the live tooth. Fluorescence, in natural dentition, is the emission of light in the blue area of the spectrum which is absorbed in the near ultraviolet; teeth are absorbing light from 320-350 nanometers and they are re-emitting light in the visible spectrum between 410-440 nanometers. This phenomenon gives teeth their pearly effect and vibrant lifelike look, in contrast with the lifeless look of extracted teeth. The light source 8 of FIG. 1 produces light having a substantial ultraviolet component; the resulting reflected light data being stored. The patient's tooth is again examined, but without the ultraviolet component, which is filtered out by, for example, substituting a glass fiber for the quartz fiber of cable 9 and actuating source 8. Alternatively, a filter may be employed. The difference between these two measurements will indicate the degree of fluorescence of the live tooth under examination. The resulting factor is added to the search in the computer and may be employed if over a given value to address a look-up table which indicates the amount of fluorescent material to be added to the recipe pursuant to the value of the fluorescence factor; the greater the value of the factor, the greater the amount of fluorescent material to be added.

In summary, a recipe is calculated in terms of concentrations of specific porcelain colorants which are to be mixed with a base porcelain medium to obtain the shade that most closely matches that of the patient's natural dentition under various lighting conditions. The visual matching is further enhanced through the use of measuring fluorescence and translucency of the patient's tooth.

The color search and match routines employed by the computer are known in the art and further reference may be made to U.S. Pat. No. 3,935,436, incorporated by reference, which illustrates a detailed flow chart in FIG. 8 and includes a program listing twenty-five pages in length. Thus, further details of the color matching program have been omitted in the interests of clarity, brevity and economy. Further reference may be made to U.S. Pat. Nos. 3,778,541 and 3,878,384 issued to Kent Bowker, which describes a system for scanning a color photograph and searching in color space for those shades closest to the scanned shades to automatically produce data indicating particular paint pigments used to accurately reproduce each shade scanned by the computer. For further information on the employment of integrating spheres in a matching color system, see U.S. Pat. No. 3,935,436.

In the prototype system constructed by the inventor, an Intel 8086 16-bit single board computer having 64 K RAM program storage was employed, together with a floppy disc store having a capacity of up to 500 K bytes. A 20-column printer for recipe output was employed.

While preferred steps in carrying out the present invention have been explained, it should be apparent that other equivalent steps may be utilized within the scope of the present invention, which is to be restricted only by a reasonable interpretation of the following claims:

The invention claimed is:

1. A method of determining shade values for a recipe used to fabricate a color matched replica of a live tooth being examined in the mouth of a patient, comprising the steps of:
   (a) directing polychromatic light at the surface of said live tooth;
   (b) recording dental color data of light reflected from said live tooth consisting of a plurality of values indicative of the power distribution of wavelengths of light reflected from said tooth within each of a plurality of frequency bands in response to the execution of step (a);
   (c) operating upon the color data produced in accordance with step (b) with the power distribution values of a given standard illuminant to produce modified color data;
   (d) converting the modified color data produced in accordance with Step (c) to three tristimulus values by multiplying said modified color data with three standard color data templates;
   (e) comparing said three tristimulus values with color values of a group of stored main color dental shades in accordance with a first level search;
   (f) establishing an acceptance color difference tolerance value; and
   (g) identifying stored main color shades which are close enough to the shade represented by said three tristimulus values to satisfy said tolerance value.

2. The method of claim 1 further including repeating Step (e) to produce a second level search if no match is produced by executing Step (e), by comparing said three tristimulus values with a second, substantially larger group of stored dental color shades.

3. The method of claim 2 further including the step of increasing said tolerance value if a match is not produced by carrying out said second level search.

4. The method of claim 2 further including the step of modifying a stored color shade value to bring it within said tolerance value if no match is produced.

5. The method of claim 1 further including the step of modifying a stored color shade value to bring it within said tolerance value if no match is produced.

6. The method as set forth in claims 1, 2, 3, 4, or 5, further including the step of checking for least metamerism in the event that at least two color data matches are produced, by operating upon said three tristimulus values with additional illumination standards other than said given standard illuminant to produce modified tristimulus values;
   matching said modified tristimulus values with reflectance color data of the previously matched shades determined under said additional illumintion standards; and
   determining which matched shade produces the least color difference.

7. The method set forth in claims 1, 2, 3, 4, or 5, further including the step of:
   (h) illuminating said tooth with a dark background behind said tooth;
   (i) recording the reflected dark background color data resulting from Step (h);
   (j) subtracting said dark background color data from data recorded in accordance with step (b) to produce a translucency factor assignable to search; and
   (k) employing said translucency factor to reduce the opacity factor data component of a matched recipe should said translucency factor exceed a predetermined value.

8. The method of claims 1, 2, 3, 4, or 5, further including the steps of:
   (h) illuminating said tooth with light having a substantial ultraviolet component;
   (i) deriving a fluorescence factor by subtracting the color data produced in accordance with Step (h) from data produced by illuminating said tooth with light not including said substantial ultraviolet component; and
   (j) producing data indicative of the amount of a given fluorescent ingredient to be added to the receipe proportional to said fluoresence factor.

9. A method of determining shade values for a recipe used to fabricate a color matched replica of a live tooth being examined in the mouth of a patient, comprising the steps of:

(a) applying polychromatic light to the surface of a color calibration chip;

(b) recording color signature data consisting of a plurality of values indicative of the power distribution of wavelengths of light reflected from said chip within each of a plurality of frequency bands in response to reflection of light from said calibration chip in accordance with executing step (a);

(c) enabling the normalization of subsequent dental color data measurements by applying a correction factor thereto produced by subtracting data recorded in accordance with step (b) from a stored set of data representing the calibration of the stored dental color data base;

(d) directing polychromatic light at the surface of said live tooth;

(e) recording dental color data of light reflected from said live tooth in response to the execution of Step (d);

(f) normalizing dental color data recorded in accordance with Step (e) by applying said correction factor thereto, said correction factor produced in accordance with Step (c);

(g) operating upon the color data produced in accordance with Step (f) with the power distribution values of a given standard illuminant to produce modified color data;

(h) converting the modified color data produced in accordance with Step (g) to three tristimulus values by multiplying said modified color data with three standard color data templates;

(i) comparing said three tristimulus values with color values of a group of stored main color dental shades in accordance with a first level search;

(j) establishing an acceptable color difference tolerance value; and (k) identifying stored main color shades which are close enough to the shade represented by said three tristimulus values to satisfy said tolerance value.

10. The method of claim 9 further including repeating Step (i) to produce a second level search if no match is produced by executing Step (i), by comparing said three tristimulus values with a second, substantially larger group of stored dental color shades.

11. The method of claim 10 further including the step of increasing said tolerance value if a match is not produced by said second level search.

12. The method of claim 10, further including the step of modifying a stored color shade value to bring it within said tolerance value if no match is produced.

13. The method of claim 9, further including the step of modifying a stored color shade value to bring it within said tolerance value if no match is produced.

14. The method as set forth in claims 9, 10, 11, 12, or 13, further including the step of checking for least metamerism in the event that at least two color data matches are produced, by operating upon said three tristimulus values with additional illumination standards other than the standard of Step (g) to produce modified tristimulus values;

matching said modified tristimulus values with reflectance color data of the previously matched shades determined under said additional illumination standards; and determining which matched shade produces the least color difference.

15. The method set forth in claims 9, 10, 11, 12, or 13, further including the step of illuminating said tooth with a dark background behind said tooth;

recording the reflected dark background color data resulting from the preceding step;

subtracting said dark background color data from data recorded in accordance with Step (e) to produce a translucency factor assignable to search; and employing said translucency factor to reduce the opacity factor data component of a matched recipe should said translucency factor exceed a predetermined value.

16. The method of claims 9, 10, 11, 12, or 13, further including the step of illuminating said tooth with light having a substantial ultraviolet component;

deriving a flourescence factor by comparing the color data produced in accordance with the preceding step with data produced by illuminating said tooth with light not including said substantial ultraviolet component; and producing data indicative of the amount of a given fluorescent ingredient to be added to the recipe proportional to said fluorescence factor.

17. A method of determining shade values for a recipe used to fabricate a color matched replica of a live tooth being examined in the mouth of a patient, comprising the steps of:

(a) directing polychromatic light to the surface of a color calibration chip;

(b) recording color signature data consisting of a plurality of values indicative of the power distribution of wavelengths of light reflected from said chip within each of a plurality of frequency bands in response to reflection of light from said calibration chip in accordance with Step (a);

(c) enabling the normalization of subsequent dental color data measurements by applying a correction factor thereto produced by subtracting data recorded in accordance with Step (b) from a stored set of data representing the calibration of the stored dental color data base;

(d) directing polychromatic light at the surface of said live tooth;

(e) recording dental color data of light reflected from said live tooth in response to the execution of step (d);

(f) normalizing dental color data recorded in accordance with step (e) by applying said correction factor thereto, said correction factor produced in accordance with step (c);

(g) operating upon the color data produced in accordance with Step (f) with the power distribution values of a given standard illuminant to produce modified color data;

(h) converting the modified color data produced in accordance with step (g) to three tristimulus values by multiplying said modified color data with three standard color data templates;

(i) comparing said three tristimulus values with color values of a group of stored main color dental shades;

(j) establishing an acceptable color difference tolerance value;

(k) identifying stored main color shades which are close enough to the shade represented by said three tristimulus values to satisfy said tolerance value;

(l) illuminating said tooth with a dark background behind said tooth;

(m) recording the reflected dark background color resulting from the preceding step;

(n) subtracting said dark background color data from data recorded in accordance with Step (e) to produce translucency factor assignable to search;

(o) employing said translucency factor to reduce the opacity factor data component of a matched recipe should said translucency factor exceed a predetermined value;

(p) illuminating said tooth with light having a substantial ultraviolet component;

(q) deriving a flourescence factor by comparing the color data produced in accordance with step (p) with data produced by illuminating said tooth with light not including said substantial ultraviolet component; and (r) producing data indicative of the amount of a given fluorescent ingredient to be added to the recipe proportional to said fluorescence factor.

18. The method as set forth in claim 17, further including the step of checking for least metamerism in the event that at least two color data matches are produced, by operating upon said three tristimulus values with additional illumination standards other than the standard of Step (g) to produce modified tristimulus values;

matching said modified tristimulus values with reflectance color data of the previously matched shades determined under said additional illumination standards; and determining which matched shade produces the least color difference.

19. The method of claim 17 or 18, further including the step of modifying a stored color shade value to bring it within said tolerance value if no match is produced.

20. A method of determining shade values for a recipe used to fabricate a color matched replica of a live tooth being examined in the mouth of a patient, comprising the steps of:

(a) directing light at the surface of said live tooth having a plurality of frequency bands;

(b) electronically producing analog signals consisting of a plurality of analog values indicative of the power distribution of wavelengths of light reflected from said live tooth within each of said plurality of frequency bands in response to the execution of step (a);

(c) electronically converting said analog signals to digital color data;

(d) providing sets of electronically stored digital shade value data;

(e) comparing said digital color data with each set of said stored digital shade value data;

(f) establishing an acceptacne color difference tolerance value for the difference between said digital color data and said stored digital shade value data;

(g) identifying those sets of stored digital shade value data which are close enough to the shade represented by said digital color data to satisfy said tolerance value;

(h) illuminating said tooth with a dark background behind said tooth;

(i) recording the reflected dark background color data resulting from step (h);

(j) substracting said dark backgound color data from data recorded in accordance with step (b) to produce a translucency factor assignable to search; and (k) employing said translucency factor to reduce the opacity factor data component of a matched recipe should said translucency factor exceed a predetermined value.

21. A method of determining shade values for a recipe used to fabricate a color matched replica of a live tooth being examined in the mouth of a patient, comprising the steps of:

(a) directing light at the surface of said live tooth having a plurality of frequency bands;

(b) electronically producing analog signals consisting of a plurality of analog values indicative of the power distribution of wavelengths of light reflected from said live tooth within each of said plurality of frequency bands in response to the execution of step (a);

(c) electronically converting said analog signals to digital color data;

(d) providing sets of electronically stored digital shade value data;

(e) comparing said digital color data with each set of said stored digital shade value data;

(f) establishing an acceptance color difference tolerance value for the difference between said digital color data and said stored digital shade value data;

(g) identifying those sets of stored digital shade value data which are close enough to the shade represented by said digital color data to satisfy said tolerance value;

(h) illuminating said tooth with light having a substantial ultraviolet component;

(i) deriving a fluorescence factor by subtracting the color data produced in accordance with step (h) from data produced by illuminating said tooth with light not including said substantial ultraviolet component; and (j) producing data indicative of the amount of a given fluorescent ingredient to be added to the receipe proportional to said flouresence factor.

* * * * *